United States Patent [19]

Allenger et al.

[11] Patent Number: 4,973,776

[45] Date of Patent: Nov. 27, 1990

[54] CONVERSION OF METHANE TO GASOLINE-RANGE HYDROCARBONS VIA ISOBUTENE

[75] Inventors: Vincenza M. Allenger, Kanata; Raj N. Pandey, Guelph, both of Canada

[73] Assignee: Energy, Mines & Resources - Canada, Ottawa, Canada

[21] Appl. No.: 448,972

[22] Filed: Dec. 12, 1989

[30] Foreign Application Priority Data

Dec. 22, 1988 [CA] Canada .................................. 586898

[51] Int. Cl.$^5$ .......................... C07C 4/00; C07C 5/00; C07C 2/04; C07C 2/02
[52] U.S. Cl. .................................. 585/310; 585/329; 585/510; 585/530; 585/415; 585/419; 585/943
[58] Field of Search ............... 585/310, 329, 510, 530, 585/415, 419, 943

[56] References Cited

U.S. PATENT DOCUMENTS

| | | | |
|---|---|---|---|
| 19,500 | 4/1931 | Youker | 196/10 |
| 2,104,296 | 3/1935 | Frey | 196/10 |
| 2,781,409 | 3/1952 | Hepp et al. | 260/683.4 |
| 3,452,113 | 2/1967 | Godin | 260/677 |
| 3,708,553 | 1/1973 | Olah | 260/683.47 |
| 3,760,024 | 9/1973 | Cattanach | 585/415 |
| 3,845,150 | 10/1974 | Yan et al. | 585/415 |
| 4,180,689 | 12/1979 | Davies et al. | 585/415 |
| 4,291,182 | 9/1981 | Dautzenberg et al. | 585/415 |
| 4,433,192 | 2/1984 | Olah | 585/627 |
| 4,465,893 | 8/1984 | Olah | 585/500 |
| 4,467,130 | 8/1984 | Olah | 585/500 |
| 4,513,164 | 4/1985 | Olah | 585/500 |
| 4,567,307 | 1/1986 | Jones et al. | 585/330 |
| 4,665,245 | 5/1987 | Quann | 585/316 |
| 4,709,108 | 11/1987 | Devries et al. | 585/415 |
| 4,714,796 | 12/1987 | Senkan | 585/328 |
| 4,721,828 | 1/1988 | Withers | 585/500 |
| 4,727,205 | 2/1988 | Velényi et al. | 585/407 |

*Primary Examiner*—H. M. Sneed
*Assistant Examiner*—James Saba

[57] ABSTRACT

A process is described for the gas-phase condensation of natural gas or methane into gasoline-range hydrocarbons comprising the steps of: (a) reacting a mixture of methane and acetylene in the presence of a solid superacid catalyst to form isobutene, and (b) converting the isobutene product into gasoline-range hydrocarbons in the presence of a crystalline silicate zeolite catalyst.

3 Claims, No Drawings

CONVERSION OF METHANE TO GASOLINE-RANGE HYDROCARBONS VIA ISOBUTENE

BACKGROUND OF THE INVENTION

This invention relates to the synthesis of hydrocarbons from a methane source and, more particularly, to a method for converting natural gas to gasoline-range hydrocarbons.

The composition of natural gas at the wellhead varies quite widely, but the major hydrocarbon present is methane. For example, the methane content of natural gas may vary within the range from about 40 to about 95 volume %. Other constituents of natural gas include ethane, propane, butane, pentane, hydrogen sulfide, carbon dioxide, helium and nitrogen.

Two of the typical methods normally used to synthesize gasoline from natural gas require the initial step of steam reforming to produce synthesis gas, i.e. a mixture of CO and $H_2$. In the Fischer-Tropsch route, the synthesis gas is reacted over an iron catalyst to give a wide spectrum of products from light gases to waxes, with gasoline comprising only a small fraction of the products. In the methanol to gasoline route, the synthesis gas is first converted to methanol, which is further converted over an acidic zeolite catalyst to produce hydrocarbons in the gasoline range.

The alkylation of methane and olefins (alkynes) has received considerable attention since Olah, U.S. Pat. No. 4,433,192 described the alkylation between methane and ethylene over a solid superacid catalyst.

The upgrading of alkane-alkene mixtures such as isobutane with isobutene or any other $C_4$ olefin by alkylation or oligomerization to gasoline-range components, e.g. $C_8$ alkylate, is well known in the petrochemical industry. These reactions are acid catalyzed and employ HF and $H_2SO_4$ catalysts. Until recently, the alkylation of lower alkanes with alkenes has been studied in liquid acid media and liquid phase reaction conditions were considered to substantially limit practical application of the reaction. In addition, the products were a mixture of oily oligomers having molecular weights from about 100 to 700.

Numerous patents describe the oligomerization, alkylation and aromatization of alkanes, e.g. ethane, propane and butane and alkenes, e.g. ethene, propene and butene. Medium and large pore zeolites, e.g. ZSM-3, ZSM-5, ZSM-18, ZSM-20, faujasite, mordenite and type Y in their hydrogen and rareearth exchanged forms, are used for this purpose. For instance, conversion of olefins to gasoline and/or distillate products is disclosed in U.S. Pat. Nos. 3,960,764 and 4,021,502, in which gaseous olefins in the range of ethylene to pentene, either alone or in admixture with paraffins, are converted into an olefinic gasoline blending stock by contacting the olefins with a catalyst bed made up of ZSM-5 zeolite.

It is the object of the present invention to provide a simple and inexpensive two-stage method for converting natural gas to gasoline-range hydrocarbons.

SUMMARY OF THE INVENTION

According to the present invention it has been found that a greatly improved process for synthesizing gasoline from natural gas comprises a 2-stage procedure in which isobutene is formed as an intermediate. Thus, the invention in its broadest aspect relates to a process for the gas-phase condensation of natural gas or methane into gasoline-range hydrocarbons by the steps of: (a) reacting a mixture of methane and acetylene in the presence of a solid superacid catalyst to form isobutene, and (b) converting the thus obtained isobutene product in the presence of a crystalline zeolite catalyst into gasoline-range hydrocarbons.

It has been found that the isobutene can be formed in a very efficient manner by reacting a mixture of methane and acetylene in the presence of a solid superacid catalyst. The methane is, of course, readily available from the natural gas, while acetylene may be derived by the pyrolysis of natural gas and coal or the reaction of calcium carbide with water.

The superacid catalysts used for the production of the isobutene are of the general type described in U.S. Pat. No. 4,465,893 and these are typically solid superacid halides of metals of Groups IV, V or VI of the Periodic Table, supported on a carrier. They are preferably in the form of fluorides with binary metal fluorides being particularly useful, e.g. those of antimony, niobium and tantalum. Among specific preferred catalysts, there may be mentioned tantalum pentafluoride, antimony pentafluoride and niobium pentafluoride.

The reaction between the methane and acetylene may be carried out at low temperatures in the range of 0 to 100° C., preferably between 20° and 50° C. Low pressures in the range of 1 to 25 atmospheres may also be used with a range of 5 to 10 atmospheres being preferred. The feedstock preferably comprises a mixture of methane and acetylene in mole ratios of 10-10:1 of methane to acetylene. Such reaction generally produces isobutene with a high selectivity in the order of 95 mol%, the remaining 5 mol% typically comprising n-butane, 1-butene, ethane and propane.

In the second stage of the process, the effluent from the first stage is preferably used and this consists mainly of isobutene and residual methane. This effluent stream is preferably reacted over a zeolite catalyst bed maintained between 200° C. and 400° C. and a pressure between 1 and 10 atmospheres. The effluent from the second stage contains largely unreacted methane and gasoline-range hydrocarbons.

The zeolite catalyst preferred used for the second stage include the crystalline alumino silicate zeolites having a silica to alumina molar ratio of at least 12, a constraint index of from about 1 to about 12 and acid cracking activity of about 50–300. Representative of the ZSM-5 type zeolites are ZSM-5, ZSM-11, ZSM-12, ZSM-23, ZSMA-35 and ZSM-38. ZSM-5 is disclosed in U.S. Pat. No. 3,702,886 and ZSM-11 is disclosed in U.S. Pat. No. 3,709,979. Also, see U.S. Pat. No. 3,832,449 for ZSM-12; U.S. Pat. No. 4,076,842 for ZSM-23; U.S. Pat. No. 4,016,145 for ZSM-35 and U.S. Pat. No. 4,046,839 for ZSM-38.

The process is preferably carried out in a dual fixed-bed reactor, but it will be appreciated that other well-known techniques such as fluidized bed processes may be used to contact the gaseous feeds with the catalysts.

Illustrative of the invention are the following examples, set forth for the purpose of illustration only and not to be construed as limiting the scope of the invention in any manner. In the related tables where product tables are given, they have been normalized, even if not stated, to provide a total of 100% conversion.

EXAMPLE 1

A methane:acetylene feed (about 95:5 mol. ratio) containing nitrogen for analytical purposes was reacted over a series of different binary fluoride catalysts (50 wt% mixture) in a fixed bed continuous flow reactor at a temperature of 25° C., a pressure of 10 atm and a GHSV of 150. The conversion and selectivity data are given in the following table.

| Conversion and selectivity data over the screened catalysts | | | | | | | |
|---|---|---|---|---|---|---|---|
| | Conversion, mol % | | Selectivity, wt % | | | | |
| | | | | | $C_4H_{10}$ | | |
| Catalyst | $CH_4$ | $C_2H_2$ | $C_2H_6$ | $C_3H_8$ | iso | n | $i-C_4H_8$ |
| $TaF_5-AlF_3$ | 9.9 | 100 | 6.1 | 1.0 | 3.3 | 0.2 | 89.4 |
| $NbF_5-AlF_3$ | 16.0 | 100 | 2.0 | 0.6 | 2.6 | 0.2 | 94.6 |
| $SbF_5-AlF_3$ | 21.6 | 82 | 12.5 | 2.5 | 2.4 | 6.2 | 76.8 |
| $TaF_5-CF_{0.6}$ | 9.5 | 100 | 5.5 | 0.5 | 3.5 | 5.9 | 84.6 |
| $NbF_5-CF_{0.6}$ | 10.9 | 100 | 5.3 | 2.4 | 4.1 | 7.0 | 81.2 |
| $SbF_5-CF_{0.6}$ | 9.0 | 100 | 4.4 | 0.5 | 5.1 | 4.4 | 85.6 |

Run time and analysis time = 30 min.

EXAMPLE 2

The variation in the conversion and selectivity with time on stream was investigated over a $NbF_5-AlF_3$ catalyst for a feed gas of the same composition as in Example 1. The results are summarized in the following table:

| Variation in conversion and selectivity with time on stream | | | | | | | |
|---|---|---|---|---|---|---|---|
| Time on stream [h] | Conversion, mol % | | Selectivity, wt % | | | | |
| | | | | | $C_4H_{10}$ | | |
| | $CH_4$ | $C_2H_2$ | $C_2H_6$ | $C_3H_8$ | iso | n | $i-C_4H_8$ |
| initial | 23.1 | 100 | 5.1 | 1.2 | 15.6 | 0.4 | 78.1 |
| 1 | 29.2 | 100 | 3.6 | 0.4 | 2.5 | — | 93.5 |
| 2 | 27.4 | 100 | 3.9 | 0.1 | 1.1 | — | 94.9 |
| 3 | 22.9 | 92.2 | 3.8 | 0.1 | 1.1 | — | 95.0 |
| 4 | 23.3 | 95.5 | 2.8 | 0.2 | 0.5 | — | 96.5 |
| 5 | 12.2 | 70 | 2.6 | 0.8 | 0.2 | — | 96.4 |

— not detected

EXAMPLE 3

A fixed-bed reactor assembly was used for testing the second stage of the present invention. The feed was a mixture of 15 mol.% isobutene in helium to the second reactor which was loaded with H-ZSM-5. The reaction was carried out at a temperature of 250° C., a pressure of 1 atm and a WHSV of 0.5 $h^{+1}$. The conversion and selectivity data for isobutene are given in the following table:

| Conversion of isobutene over H-ZSM-5 | | | | | |
|---|---|---|---|---|---|
| Conversion, mol % | Selectivity, wt % | | | | |
| $C_4H_8$ | $CH_4$ | $C_2$ | $C_3$ | $C_4$ | $C_5+$ |
| 100 | tr | 0.2 | 17.6 | 37.2 | 45 | tr trace
$C_2$ consists mostly of ethane
$C_3$ consists of propane and propylene
$C_4$ excludes isobutene It is evident from the above results that gasoline-range hydrocarbons ($C_5+$) constitute a large proportion of the product.

EXAMPLE 4

For the second stage of the process, a comparison was made between isobutene as a feedstock and other $C_4$ feedstocks. Isobutane and N-butane were used as feedstocks at various operating conditions and those operating conditions and reaction results using a ZSM-5 catalyst are shown in the table below:

| A Comparision of the reactivity and selectivity of various $C_4$ hydrocarbon feeds over ZSM-5 (15 mol % $C_4$ hydrocarbon in He) | | | | | | | |
|---|---|---|---|---|---|---|---|
| Hydrocarbon | Temp (°C.) | Conversion, mol % | Selectivity, wt % | | | | |
| | | | $CH_4$ | $C_2H_4$ | $C_3H_8$ | $C_4$ | $C_5+$ |
| isobutane | 300 | 39 | 0.2 | 0.7 | 49.1 | 20.0 | 30.0 |
| isobutane | 359 | 75 | 1.6 | 3.2 | 76.4 | 11.8 | 7.0 |
| n-butane | 304 | 55 | 0.2 | 1.0 | 70.0 | 18.8 | 10.0 |
| n-butane | 360 | 91 | 1.9 | 4.4 | 83.2 | 8.5 | 2.0 |

Comparing the results of Examples 3 and 4, it will be seen that a much lower operating temperature can be used when the feedstock consists mainly of isobutene. Improvements in the $C_5+$ hydrocarbon selectivity is also evident with the isobutene feed. At higher temperatures, the $C_5+$ hydrocarbon selectivity was found to decrease significantly, and this is believed to be due to secondary reactions such as cracking.

The high conversion of the alkyne in the first stage of the process and the low reactivity at the operating conditions for the second stage for other $C_4$ hydrocarbons contained in the product steam from stage 1 indicates that little if any interstage separation is necessary.

We claim:

1. A process for the gas-phase condensation of natural gas or methane into gasoline-range hydrocarbons comprising the steps of:
   (a) reacting a mixture of methane and acetylene at a temperature of about 20°–50° C. and a pressure of about 1–25 atm. in the presence of a solid superacid catalyst which comprises a binary metal fluoride, in which one component is selected from tantalum pentafluoride, antimony pentafluoride and niobium pentafluoride and the other component is selected from anhydrous aluminum trifluoride and $CF_{0.6}$, to form isobutene, and
   (b) converting the isobutene product obtained at a temperature of about 200–400° C. and a pressure of 1–10 atm in the presence of a crystalline silicate zeolite catalyst into gasoline-range hydrocarbons.

2. A process according to claim 1 wherein the zeolite catalyst contains at least one of Fe, Zn, Cu, Pt, Ga and Ge.

3. A process according to claim 1 wherein the zeolite catalyst is HZSM-5.1

* * * * *